(12) United States Patent
Yoshimura et al.

(10) Patent No.: US 7,338,172 B2
(45) Date of Patent: Mar. 4, 2008

(54) OPHTHALMIC APPARATUS

(75) Inventors: Kazuhiro Yoshimura, Toyohashi (JP); Akihiro Hayashi, Toyokawa (JP)

(73) Assignee: Nidek Co., Ltd., Gamagori (JP)

( * ) Notice: Subject to any disclaimer, the term of this patent is extended or adjusted under 35 U.S.C. 154(b) by 313 days.

(21) Appl. No.: 11/050,962

(22) Filed: Feb. 7, 2005

(65) Prior Publication Data
US 2005/0185137 A1    Aug. 25, 2005

(30) Foreign Application Priority Data
Feb. 10, 2004 (JP) .............................. 2004-032850

(51) Int. Cl.
*A61B 3/14* (2006.01)
*A61B 3/00* (2006.01)
(52) U.S. Cl. ...................... 351/245; 351/208
(58) Field of Classification Search ................ 351/208, 351/245
See application file for complete search history.

(56) References Cited
U.S. PATENT DOCUMENTS
5,644,375 A * 7/1997 Suzuki ........................ 351/208
5,910,833 A * 6/1999 Iijima ......................... 351/208
2004/0189936 A1* 9/2004 Mimura et al. .............. 351/205

FOREIGN PATENT DOCUMENTS
JP        Y2 2517466        8/1996

* cited by examiner

*Primary Examiner*—Jordan Schwartz
*Assistant Examiner*—James C Jones
(74) *Attorney, Agent, or Firm*—Oliff & Berridge, PLC

(57) ABSTRACT

An ophthalmic apparatus comprises: a base; an examination part which includes an optical system for examining an eye of a patient and is placed to be movable horizontally on the base; and a fixing mechanism provided in the examination part and arranged to fix the examination part on the base; wherein the fixing mechanism comprises: an arm pivotally mounted to be turned in an up and down directions; a fixing member which is supported by the arm so that it is brought in contact with the base by downward turning of the arm and it is separated from the base by upward turning of the arm, the fixing member having large friction with respect to the base; and an operating member for turning the arm in the up and down directions, the operating member having a longer distance from a turning center of the arm to a position of the operating member than a distance from the turning center of the arm to a position of the fixing member.

7 Claims, 4 Drawing Sheets

OPHTHALMIC APPARATUS

BACKGROUND OF THE INVENTION

1. Field of the Invention

The present invention relates to an ophthalmic apparatus for examining (including observing, measuring, photographing, and others) an eye.

2. Description of Related Art

As an ophthalmic apparatus, there are various apparatuses such as a slit lamp microscope for observing an eye, a refractometer for objectively measuring eye refractive power of an eye, a keratometer for measuring the shape of a cornea, a tonometer for measuring intraocular pressure in noncontact with an eye, a fundus camera for photographing the fundus of an eye. Each of these apparatuses is provided with an examination part in which an examining optical system is placed, a base on which the examination part is mounted, a movement mechanism for horizontally moving the examination part on the base, and a fixing mechanism for fixing the examination part on the base against horizontal movement. Such fixing mechanism generally uses a fixing screw (bolt) to fix the examination part on the base.

In fixing the examination part on the base with a screw, a user (examiner) has to turn the screw a number of times and further tighten the screw for secure fixation. Furthermore, for releasing the examination part from the base, the user has to loosen the screw.

SUMMARY OF THE INVENTION

The present invention has been made in view of the above circumstances and has an object to provide an ophthalmic apparatus capable of fixing an examination part on a base securely by a simple operation.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an ophthalmic apparatus comprising: a base; an examination part which includes an optical system for examining an eye of a patient and is placed to be movable horizontally on the base; and a fixing mechanism provided in the examination part and arranged to fix the examination part on the base; wherein the fixing mechanism comprises: an arm pivotally mounted to be turned in an up and down directions; a firing member which is supported by the arm so that it is brought in contact with the base by downward turning of the arm and it is separated from the base by upward turning of the arm, the fixing member having large friction with respect to the base; and an operating member for turning the arm in the up and down directions, the operating member having a longer distance from a turning center of the arm to a position of the operating member than a distance from the turning center of the arm to a position of the fixing member.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
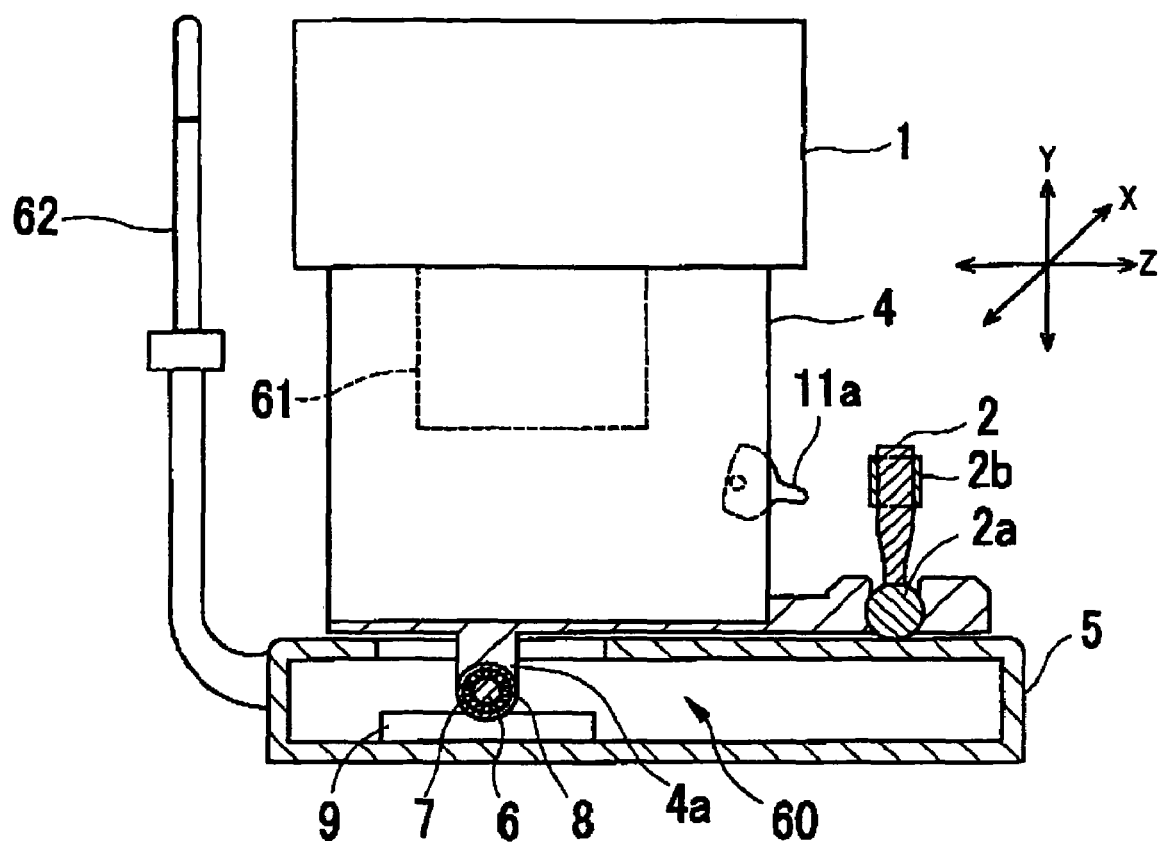
FIG. 1 is a side view showing, partially in section, a schematic structure of an ophthalmic apparatus in an embodiment of the present invention.

A detailed description of a preferred embodiment of the present invention will now be given referring to the accompanying drawings. FIG. 1 is a side view showing, partially in section, a schematic structure of an ophthalmic apparatus in the present embodiment. An examination unit 1 includes an optical system for examining (including observing, measuring, photographing, and others) an eye of a patient (an examinee) is mounted on a base 5 through a moving carriage 4. The moving carriage 4 and the base 5 are provided with a movement mechanism 60 (mentioned later in detail) including a joystick 2 serving as an operating member. When this joystick 2 is inclined right/left and forward/backward (hereinafter, an X-direction and Z-direction), the moving carriage 4 is moved horizontally on the base 5 in the X- and Z-directions by the movement mechanism 60, thereby moving the examination unit 1 horizontally on the base 5 in the X- and Z-directions. The moving carriage 4 is also provided with a movement mechanism 61 for moving the examination unit 1 up/down (hereinafter, a Y-direction) with respect to the moving carriage 4. By rotation of a knob 2b of the joystick 2, the examination unit 1 is moved in the Y-direction by the movement mechanism 61 based on a rotation signal from the knob 2b.

The movement mechanism 60 includes the joystick 2, a steel ball 2a provided at a bottom of the joystick 2, an axle 6 inserted, through a bearing (steel ball) 8, in a guide pipe 7 that is provided extending in the X-direction in a protruding portion 4a of the moving carriage 4 at a side facing the base 5, i.e., a bottom side, a pair of pinions not shown provided at both ends of the axle 8, a pair of racks 9 that are provided on a bottom plate of the base 5 and engage with the pinions, and others. With this structure, the moving carriage 4 can be moved horizontally in the X- and Z-directions with respect to the base 5. A head support part 62 for fixedly supporting the face (head) of the patient is secured to the base 5.

Figure 2:
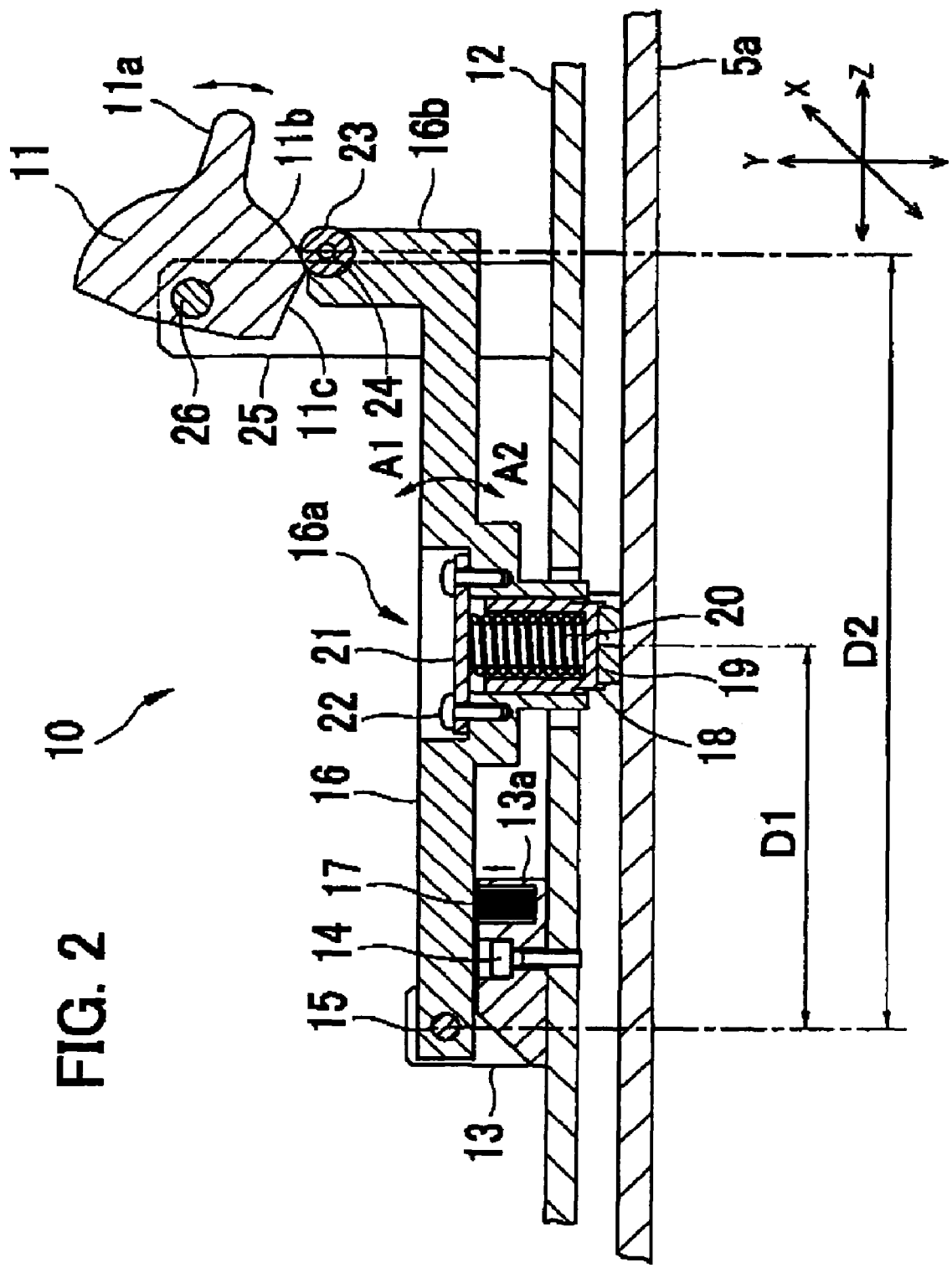
FIG. 2 is a sectional view showing a schematic structure of a fixing mechanism.

The following explanation is made on a fixing mechanism 10 for fixing the moving carriage 4 (the examination unit 1) on the base 5 against horizontal movement in the X- and Z-directions, referring to FIG. 2. An arm supporting base 18 is secured on an inner face of a bottom plate 12 of the moving carriage 4 with a screw 14. A shaft 15 extending in the X-direction is secured to the supporting base 13. An arm 16 extending in the Z-direction is pivotally mounted on the shaft 15 so as to be turned around the shaft 15 in directions indicated by arrows A1 and A2. A spring 17 is assembled in a compressed state in a recess 13a of the supporting base 13. By a returning (expanding) force of the spring 17, the arm 16 is urged upward (toward the examination unit 1). In a groove 16a formed in the arm 16 at substantially a center thereof, a moving supporting base 18 including a fixing member 19 at its bottom is fit to be movable in an up and down directions with respect to the arm 16. The fixing member 19 provides large friction with respect to a top plate 5a of the base 5. In the supporting base 18, a spring 20 is assembled in a compressed state by a cover 21 and screws 22. By a returning (expanding) force of the spring 20, the fixing member 19 is urged downward (toward the base 5). This spring 20 is designed such that the downward urging force is a smaller spring force within an operating range than total gravity of the examination unit 1 and the moving carriage 4, and the fixing member 19 can provide a braking force enough for fixing the moving carriage 4 by friction with respect to the top plate 5a.

A shaft 24 extending in the X-direction is secured to an end 16b of the arm 16. A roller 23 is rotatably supported on the shaft 24. A cam supporting base 25 is secured on the bottom plate 12. A shaft 26 extending in the X-direction is secured to the supporting base 25. On the shaft 26, a cam 11 having an operating lever 11a is supported rotatably in the same direction as the turning direction of the arm 16. The cam 11 is provided with a curved surface 11b (a first surface) which has a uniform distance from a central axis of the shaft 26 and a flat surface 11c (a second surface) which has a shorter distance from the central axis of the shaft 26 than the distance from the central axis of the shaft 26 to the curved surface 11b.

The operation of the filing mechanism 10 to fix or release the moving carriage 4 will be described below. For releasing the fixing of the moving carriage 4, thereby enabling the horizontal movement of the moving carriage 4 in the X- and Z-directions, an examiner turns the lever 11a up. When this lever 11a is turned up, the arm 16 is turned (raised) in the direction A1 by the upward urging force of the spring 17 until the roller 23 comes into contact with the flat surface 11c of the cam 11. At this time, the cam 11 has a tendency to further rotate upward (counterclockwise in FIG. 2) by turning (rising) of the arm 16, but this is prevented by a limit plate not shown. Thus the cam 11 is fixed without further rotating upward even after the examiner takes his hand off the lever 11a. Consequently, the turning of the arm 16 is limited. In this state, the fixing member 19 is separated from the base 5 (a first position), thereby releasing the fixing of the moving carriage 4. Thereafter, when the examiner inclines the joystick 2, the moving carriage 4 and the examination unit 1 are integrally moved horizontally in the X- and Z-directions by the moving mechanism 60.

To fix the moving carriage 4, thereby disabling the horizontal movement of the moving carriage 4 in the X- and Z-directions, the examiner turns the lever 11a down. When the lever 11a is turned down, the curved surface 11b of the cam 11 pushes the roller 23 downward, turning (lowering) the arm 16 in the direction A2 against the upward urging force of the spring 17. Thus, the spring 20 is compressed, producing the downward urging force, which pressing the fixing member 19 against the base 5 (a second position). Accordingly, the moving carriage 4 is fixed in position by friction between the fixing member 19 and the base 5. By the upward urging force of the spring 17, the roller 23 is brought in contact with the curved surface 11b of the cam 11. Because the curved surface 11b is a segment of a circle having a uniform radius from the rotation center of the cam 11 (the central axis of the shaft 26) and the roller 23 can move only in a circular path about the shaft 15, the cam 11 is fixedly held without rotating even after the examiner takes his hand off the lever 11a. Accordingly, the turning of the arm 16 is limited.

The fixing-member 19 is arranged to be pressed against the base 5 by the downward urging force of the spring 20. This makes it possible to eliminate the need for controlling a degree of pressing the fixing member 19, as compared with the case where the fixing member 19 is pressed against the base 5 without the use of the spring 20. Further, the pressing force exerted on the fixing member 19 will not vary from one apparatus to another. Consequently, the moving carriage 4 can be firmly fixed by the substantially constant pressing force.

If the downward urging force of the spring 20 is set as a larger force within the operating range of the spring 20 than the total gravity of the examination unit 1 and the moving carriage 4, the force for turning up the lever 11a will be required to be the total gravity or more. In the above description, however, the downward urging force of the spring 20 is set to be the total gravity or less, which can prevent such undesirable situation.

The apparatus utilizes the action of a lever (leverage) assuming that the shaft 15 is a fulcrum, the end 16b of the arm 16 (the roller 23) is a point of the lever to which force is applied (a power point), and the fixing member 19 is a working point. A distance D2 from the shaft 15 serving as the fulcrum to the end 16b serving as the power point is determined to be longer than a distance D1 from the shaft 15 to the fixing member 19 serving as the working point. Accordingly, the lever 11a can be operated even by a small force.

Figure 3:
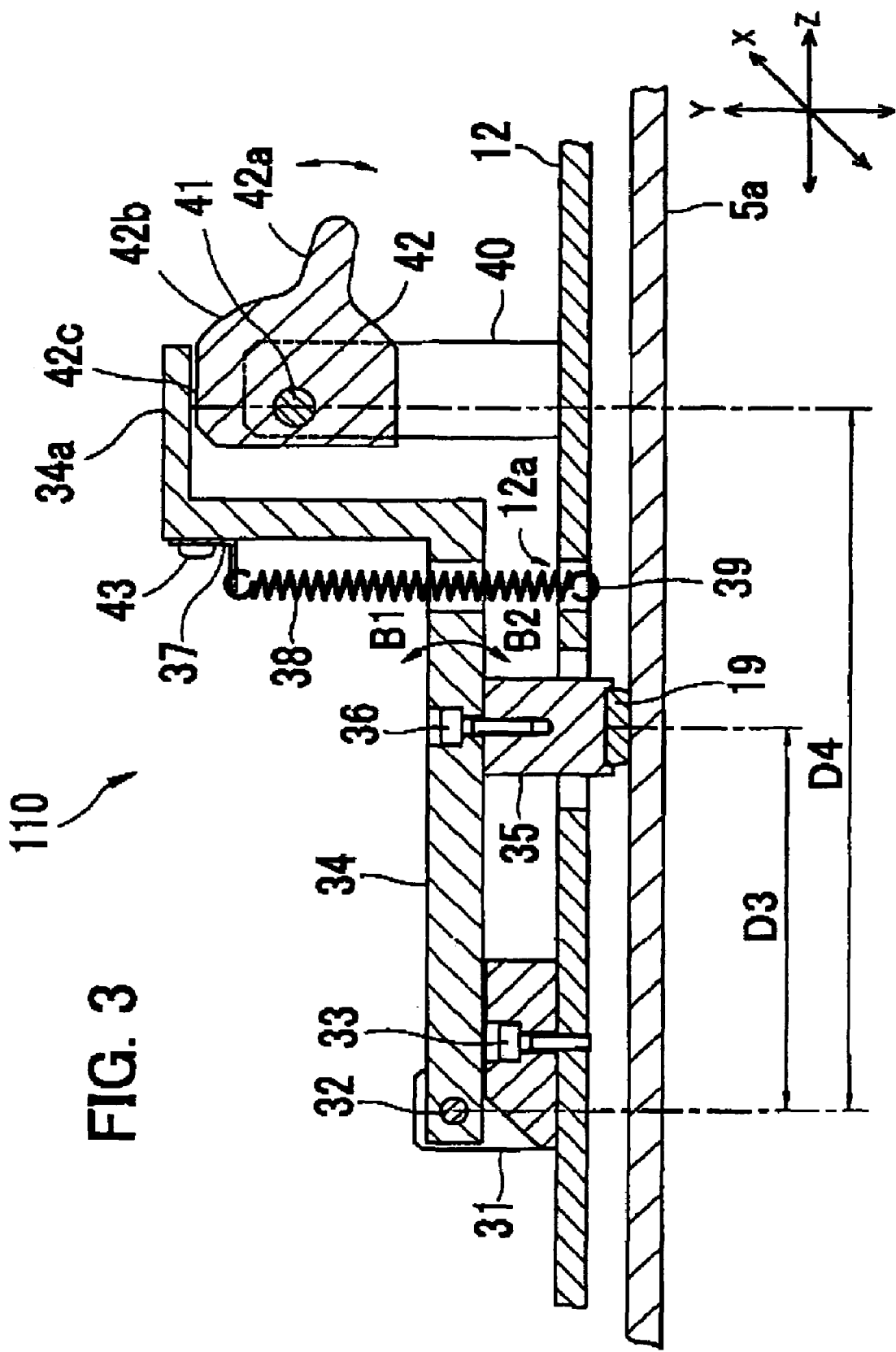
FIG. 3 is a sectional view showing a schematic structure of a first modification of the firing mechanism.

A fixing mechanism 110 in a first modification will be described below with reference to FIG. 3. Parts identical to those of the fixing mechanism 10 are indicated by the same reference numerals and their explanations are omitted herein. An arm supporting base 31 is secured on the bottom plate 12 of the moving carriage 4 with a screw 33. A shaft 32 extending in an X-direction is secured to the supporting base 31 and an arm 34 extending in a Z-direction is pivotally mounted on the shaft 32 to be turned around the shaft 32 in directions indicated by arrows B1 and B2. A supporting base 35 including the fixing member 19 at its bottom is secured to the arm 34 at substantially a center thereof with a screw 36. Further, a spring supporting base 37 for fixing one end of a spring 38 is secured on the arm 34 with a screw 43. The other end of the spring 38 in an extended state is anchored to a pin 39 through a hole 12a of the bottom plate 12. By the returning (contracting) force of the spring 38, the arm 84 is urged downward. The spring 38 is designed such that the downward urging force is a smaller spring force within an operating range than total gravity of the examination unit 1 and the moving carriage 4, and the fixing member 19 can provide a braking force enough for fixing the moving carriage 4 by friction with respect to the top plate 5a of the base 5.

A cam supporting base 40 is secured on the bottom plate 12. A shaft 41 extending in the X-direction is secured to the supporting base 40. On the shaft 41, a cam 42 having an operating lever 42a is supported rotatably in the same direction as the turning direction of the arm 34. The cam 42 is provided with a curved surface 42b (a first surface) which has a uniform distance from a central axis of the shaft 41 and a flat surface 42c (a second surface) which has a shorter distance from the central axis of the shaft 41 than the distance from the central axis of the shaft 41 to the curved surface 42b.

For releasing the firing of the moving carriage 4, an examiner turns the lever 42a up. When the lever 42a is turned up, the curved surface 42b of the cam 42 pushes an end 34a of the arm 34 upward, thereby turning (raising) the arm 34 in the direction B1 against the downward urging force of the spring 38, and thus the fixing member 19 is separated from the base 5 (a first position), thereby releasing the fixing of the moving carriage 4.

For fixing the moving carnage 4, the examiner turns the lever 42a down. When the lever 42a is turned down, the arm 34 is turned (lowered) in the direction B2 by the downward urging force of the spring 38 until the end 34a is brought in contact with the flat surface 42c of the cam 42. The fixing member 19 is pressed against the base 5 (a second position), thus fixing the moving carriage 4. The fig member 19 is arranged to be pressed against the base 5 by the downward urging force of the spring 38. Accordingly, the need for controlling a degree of pressing the fixing member 19 can be eliminated. Further, the pressing force exerted on the fixing member 19 will not vary from one apparatus to another. Consequently, the moving carriage 4 can be firmly fixed by the substantially constant pressing force.

In this first modification, the apparatus utilizes the action of a lever (leverage) assuming that the shaft 32 is a fulcrum, the end 34a of the arm 34 is a point of the lever to which force is applied (a power point), and the fixing member 19 is a working point. A distance D4 from the shaft 82 serving as the fulcrum to the end 34a serving as the power point is determined to be longer than a distance D3 from the shaft 32 to the fixing member 19 serving as the working point. Accordingly, the lever 42a can be operated even by a small force.

Figure 4:
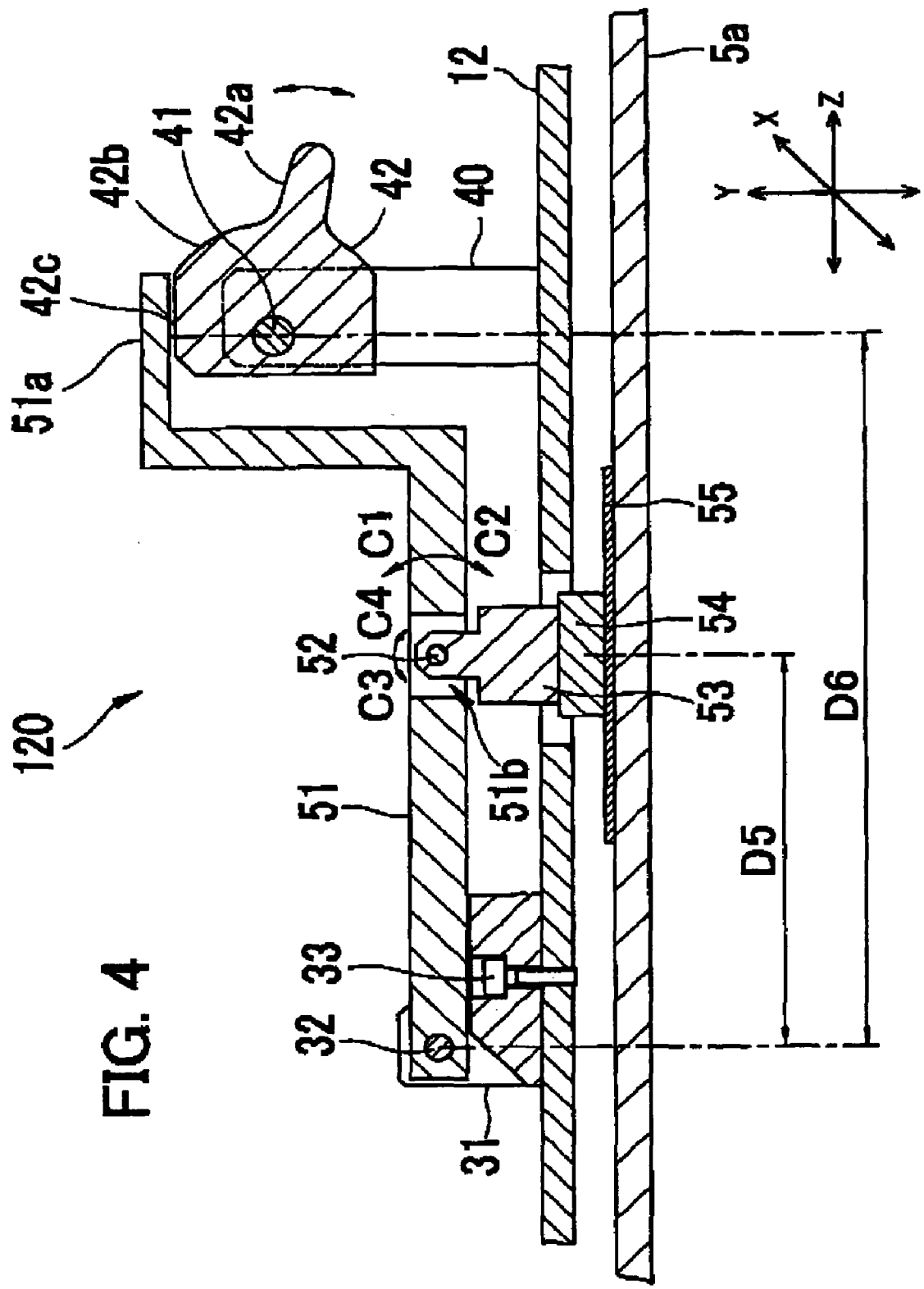
FIG. 4 is a sectional view showing a schematic structure of a second modification of the fixing mechanism.

A fixing mechanism 120 in a second modification will be described below with reference to FIG. 4. Parts identical to those of the fixing mechanism 10 or 110 are indicated by the same reference numerals and their explanations are omitted herein. An arm 51 extending in a Z-direction is pivotally mounted on the shaft 32 secured to the arm supporting base 31 so that the arm 51 is turned around the shaft 32 in directions indicated by arrows C1 and C2. A shaft 52 extending in an X-direction is secured in a hole 51a formed at substantially a center of the arm 51. On the shaft 52, a rotating supporting base 53 is supported rotatably in directions indicated by arrows C3 and C4. A magnet 54 is fixed at a bottom of the supporting base 53 to attract a steel plate 55 fixed on the top plate 5a of the base 5. This attracting force of the magnet 54 serves as a downward urging force.

For releasing the firing of the moving carriage 4, an examiner turns the lever 42a up. When the lever 42a is turned up, a curved surface 42b of a cam 42 pushes an end 51a of the arm 51 upward, thereby turning (raising) the arm 51 in the direction C1 against the downward urging force of the magnet 54, and thus the magnet 54 is separated from the steel plate 56 (a first position), thereby releasing the axing of the moving carriage 4.

For fixing the moving carriage 4, the examiner turns the lever 42a down. When the lever 42a is turned down, the arm 51 is turned (lowered) in the direction C2 by the downward urging force of the magnet 54 until the end 51a is brought in contact with the flat surface 42c of the cam 42. The magnet 54 is fixed on the steel plate 55 (a second position), fixing the moving carriage 4 on the base 5. The supporting base 53 is rotatably supported on the shaft 52 in order to bring the bottom surface of the magnet 54 in parallel with the upper surface of the steel plate 55 regardless of whether the arm 51 is turned, thereby increasing the attracting force of the magnet 54 to the steel plate 55.

In this second modification, the apparatus utilizes the action of a lever (leverage) assuming that the shaft 32 is a fulcrum, the end 51a is a point of the lever to which force is applied (a power point), and the magnet 54 is a working point. A distance D6 from the shaft 32 serving as the fulcrum to the end 51a serving as the power point is determined to be longer than a distance D5 from the shaft 32 to the magnet 54 serving as the working point. Accordingly, the lever 42a can be operated even by a small force.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An ophthalmic apparatus comprising:

a base;

an examination part which includes an optical system for examining an eye of a patient and is placed to be movable horizontally on the base; and a fixing mechanism provided in the examination part and arranged to fix the examination part on the base;

wherein the fixing mechanism comprises:

a shaft extending horizontally;

an arm pivotally mounted on the shaft to be turned in up and down directions;

a fixing member which is supported by the arm so that it is brought in contact with the base by downward turning of the arm and it is separated from the base by upward turning of the arm, the fixing member having large friction with respect to the base; and an operating member for turning the arm in the up and down directions, the operating member having a distance from the shaft serving as a turning center of the arm to a point of the arm which can come into contact with the operating member longer than a distance from the shaft to the fixing member.

2. The ophthalmic apparatus according to claim 1, wherein the examination part includes an examination unit which includes the examining optical system and a moving carriage on which the examination unit is mounted and which is placed to be movable horizontally on the base, and the fixing mechanism is provided in the moving carriage and arranged to fix the moving carriage on the base.

3. The ophthalmic apparatus according to claim 1, wherein the fixing mechanism comprises an urging member which urges the arm to turn upward, and the operating member is arranged to turn the arm downward against an upward urging force of the urging member.

4. The ophthalmic apparatus according to claim 3, wherein the fixing mechanism comprises a second urging member which urges the fixing member downward.

5. The ophthalmic apparatus according to claim 1, wherein the fixing mechanism comprises an urging member which urges the arm to turn downward, and the operating member is arranged to turn the arm upward against a downward urging force of the urging member.

6. The ophthalmic apparatus according to claim 5, wherein the urging member includes a magnet which is also used as the fixing member.

7. The ophthalmic apparatus according to claim 1, wherein the operating member includes a cam which has an operating lever and is mounted rotatably in the same direction as a turning direction of the arm, the cam including a curved surface having a uniform distance from a rotation center of the cam and a flat surface having a shorter distance from the rotation center of the cam than a distance from the rotation center to the curved surface, and the point of the arm which can come into contact with the operating member is brought in contact with the curved surface or the flat surface.

* * * * *